(12) United States Patent
Fukuura et al.

(10) Patent No.: US 9,580,735 B2
(45) Date of Patent: Feb. 28, 2017

(54) SACCHARIFYING ENZYME COMPOSITION AND METHOD FOR PRODUCING SACCHARIFIED SOLUTION USING THE SAME

(71) Applicant: HONDA MOTOR CO., LTD., Tokyo (JP)

(72) Inventors: Maiko Fukuura, Saitama (JP); Shigenobu Mitsuzawa, Saitama (JP); Migiwa Takeda, Chiba (JP); Takeshi Ara, Chiba (JP); Daisuke Shibata, Chiba (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 14/370,698

(22) PCT Filed: Dec. 27, 2012

(86) PCT No.: PCT/JP2012/083943
§ 371 (c)(1),
(2) Date: Jul. 3, 2014

(87) PCT Pub. No.: WO2013/103127
PCT Pub. Date: Jul. 11, 2013

(65) Prior Publication Data
US 2015/0044728 A1    Feb. 12, 2015

(30) Foreign Application Priority Data

Jan. 6, 2012  (JP) ................... 2012-001670

(51) Int. Cl.
| | | |
|---|---|---|
| C12P 19/14 | (2006.01) | |
| C13K 1/02 | (2006.01) | |
| C12N 9/24 | (2006.01) | |
| C12P 19/02 | (2006.01) | |

(52) U.S. Cl.
CPC ............ *C12P 19/14* (2013.01); *C12N 9/2405* (2013.01); *C12P 19/02* (2013.01); *C13K 1/02* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 8,101,393 B2 * | 1/2012 | Gray | C12N 9/2402 424/94.61 |
| 8,580,536 B2 * | 11/2013 | McBrayer | C12N 1/22 435/189 |
| 2010/0143967 A1 | 6/2010 | McFarland | |

FOREIGN PATENT DOCUMENTS

| | | |
|---|---|---|
| JP | 2001-017180 | 1/2001 |
| JP | 2010-104361 | 5/2010 |
| JP | 2010-148427 | 7/2010 |
| WO | 2011/021616 | 2/2011 |
| WO | 2011/114914 | 9/2011 |

OTHER PUBLICATIONS

Inoue et al. (Biotech. for Biofuels, 7:151, 2014, pp. 1-13).*
German Office Action dated Oct. 19, 2015 with English translation, 14 pages.
Fujii, et al. "Enzymatic Hydrolyzing Performance of Acremonium Cellulolyticus and Trichoderma Reesei Against Three Lignocellulosic Materials", 2009, Biotechnology for Biofuels 2009, 2:24, pp. 1-8.

* cited by examiner

*Primary Examiner* — Hope Robinson
(74) *Attorney, Agent, or Firm* — Rankin, Hill & Clark LLP

(57) ABSTRACT

A saccharifying enzyme composition, by which excellent saccharification performance can be attained even with a low usage thereof, as well as a method for producing a saccharified solution using the same are provided. The saccharifying enzyme composition subjects lignocellulose-based biomass as a substrate to a saccharification treatment. The saccharifying enzyme composition comprises an endoglucanase not containing a cellulose-binding domain, a cellobiohydrolase containing a cellulose-binding domain, and a β-glucosidase containing a cellulose-binding domain.

4 Claims, 6 Drawing Sheets

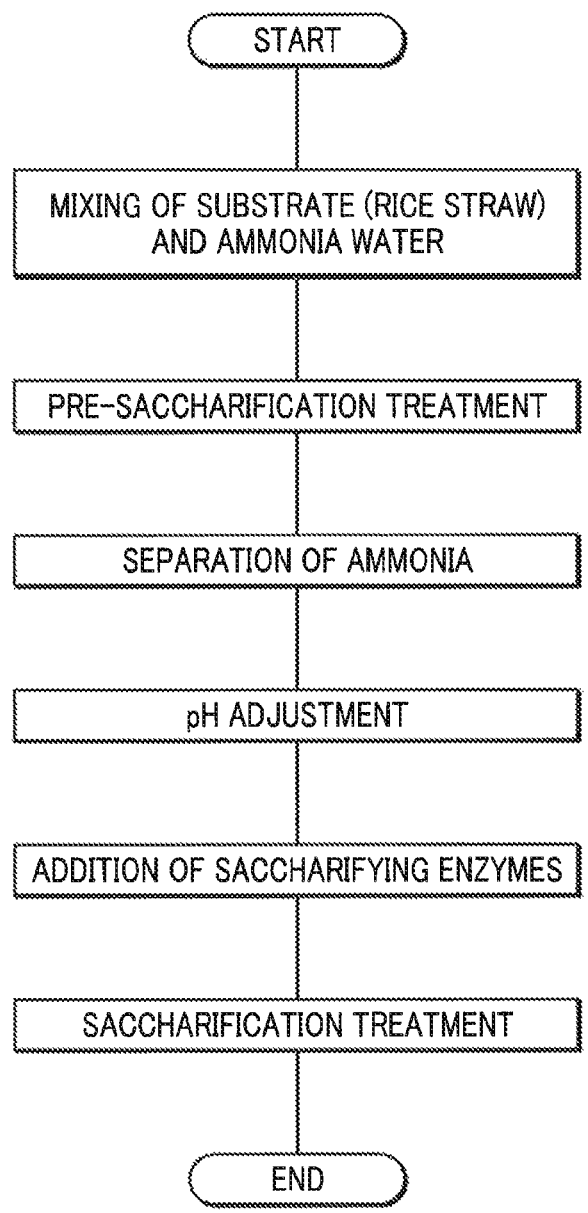

SACCHARIFYING ENZYME COMPOSITION AND METHOD FOR PRODUCING SACCHARIFIED SOLUTION USING THE SAME

This application is a U.S. national stage of PCT/JP2012/083943, filed Dec. 27, 2012, and claims priority to Japanese patent application JP 2012-001670, filed Jan. 6, 2012.

TECHNICAL FIELD

The present invention relates to a saccharifying enzyme composition and a method for producing a saccharified solution using the same.

BACKGROUND ART

A gasoline-ethanol blend fuel has been studied recently for use as an automobile fuel. By using bioethanol to be produced by fermentation and distillation of vegetable substances as the ethanol, it is believed that, if soil management is carried out strictly, a so-called carbon neutral effect can be attained to decrease the amount of carbon dioxide emission and to contribute to prevention of global warming.

However, a problem is that if farm products, such as sugarcane and maize, are used as the vegetable substances, a large amount of such farm products are consumed as a source material for ethanol, and supply of food or feed is reduced. Consequently, a technology for producing ethanol using lignocellulose-based biomass not suitable for food or feed as the vegetable substances has been studied.

Since the lignocellulose-based biomass contains cellulose, ethanol can be yielded by degrading the cellulose to glucose by a saccharification treatment using a saccharifying enzyme and fermenting the yielded glucose. As such a saccharifying enzyme, for example, a cellulase originated from *Acremonium cellulolyticus* has been heretofore known (see e.g. Patent Literature 1).

Since the saccharifying enzyme is expensive, the concentration of lignocellulose-based biomass as a substrate is set at a low level during the ethanol production in order to reduce the usage of the saccharifying enzyme. However, if the concentration of the substrate is set at a low level, the concentration of a yielded saccharified solution becomes also low, and therefore the concentration of ethanol to be yielded by fermenting the saccharified solution becomes also low. As the result, there occurs a problem that the time and thermal energy required for distillation increase, when the yielded ethanol is distilled to be concentrated.

To solve the problem, it is conceivable to increase the concentration of the substrate as well as the usage of the saccharifying enzyme to a high level, so as to yield a high concentration of ethanol, and to reduce the energy required for concentration, distillation and the like of ethanol, such that the overall energy efficiency is improved. In this case, however, since the saccharifying enzyme is expensive, a problem is that the cost increases due to the increase in the usage.

Consequently, to solve the problem, it is desired that the saccharification efficiency is maintained and at the same time the usage of a saccharifying enzyme is reduced.

CITATION LIST

Patent Literature

Patent Literature 1: Japanese Patent Laid-Open Publication No. 2010-148427

SUMMARY OF INVENTION

Technical Problem

If the total amount of saccharifying enzymes is simply reduced, however, there occurs inconvenience that the saccharification efficiency is also decreased in proportion to the amount of saccharifying enzymes.

An object of the present invention is to provide a saccharifying enzyme composition which can eliminate such inconvenience and attain superior saccharification performance with low usage thereof.

Another object of the present invention is to provide a method for producing a saccharified solution using the saccharifying enzyme composition.

Solution to Problem

By investigations of the present inventors, it has come to known that a cellulase extracted from *Acremonium cellulolyticus* is a mixture of various cellulases including those not very effective in saccharifying lignocellulose-based biomass.

Therefore, it is understood that, by simple reduction of the total amount of the cellulase mixture, cellulases with superior effectiveness in saccharifying lignocellulose-based biomass as well as cellulases without such effectiveness are decreased equally, and the saccharification efficiency is reduced in proportion to the amount of the saccharifying enzymes.

The present inventors investigated various aspects of saccharification performances of individual cellulases included in the cellulase mixture with respect to lignocellulose-based biomass. As the result, it was found that a saccharifying enzyme composition comprising a specific combination of cellulases can exhibit superior performance in saccharifying lignocellulose-based biomass, thereby completing the present invention.

Namely, according to the present invention, a saccharifying enzyme composition for subjecting lignocellulose-based biomass as a substrate to a saccharification treatment is characterized in that the saccharifying enzyme composition comprises an endoglucanase not containing a cellulose-binding domain, a cellobiohydrolase containing a cellulose-binding domain, and a β-glucosidase containing a cellulose-binding domain.

Here, the endoglucanase is a saccharifying enzyme for hydrolyzing cellulose from its internal region to a shorter-chain β-1,4-glucan. Furthermore, the cellobiohydrolase is a saccharifying enzyme for hydrolyzing cellulose or a shorter-chain β-1,4-glucan from its end to cellobiose. Furthermore, the β-glucosidase is a saccharifying enzyme for hydrolyzing cellobiose to glucoses. Meanwhile, a cellulose-binding domain means a structure which binds a saccharifying enzyme to a surface of cellulose.

With a saccharifying enzyme composition of the present invention, first the endoglucanase acts on lignocellulose-based biomass. Since the endoglucanase does not contain a cellulose-binding domain, it does not bind to a specific site of a surface of cellulose contained in the lignocellulose-based biomass as a substrate, and can contact non-specific sites over a wide range of a molecular chain of the cellulose and yield a shorter-chain β-1,4-glucan.

On the other hand, if an endoglucanase should contain a cellulose-binding domain, the endoglucanase would stay at a hydrolysis reaction field, even if it has hydrolyzed cellulose to a shorter-chain β-1,4-glucan. As the result, the chance of contact between the endoglucanase and other cellulose is reduced and the production efficiency of a shorter-chain β-1,4-glucan is decreased.

Since the cellobiohydrolase contains a cellulose-binding domain, it usually binds to cellulose and hydrolyzes the cellulose from its end to yield cellobiose, but if a shorter-chain β-1,4-glucan is present, it binds also to the shorter-chain β-1,4-glucan and hydrolyzes the same from its end to yield cellobiose. Therefore, if shorter-chain β-1,4-glucans are produced by the endoglucanase, the number of reaction initiation points for the cellobiohydrolase increases and the production of cellobioses by the cellobiohydrolase is promoted.

Further, since the β-glucosidase also contains a cellulose-binding domain, the β-glucosidase is also present in the reaction field where the cellobiohydrolase yields cellobiose. Consequently, the cellobiose yielded by the cellobiohydrolase can be immediately hydrolyzed by the β-glucosidase to glucoses.

Therefore, with a saccharifying enzyme composition of the present invention, the endoglucanase, the cellobiohydrolase and the β-glucosidase collaborate to saccharify cellulose contained in lignocellulose-based biomass as a substrate, so that the saccharification efficiency can be improved and superior saccharification performance can be attained with a low usage thereof.

The cellulose-binding domain contained in the β-glucosidase of the saccharifying enzyme composition according to the present invention is preferably composed of an amino acid sequence that has a homology of not less than 70% to an amino acid sequence of the cellulose-binding domain contained in the cellobiohydrolase.

The higher the homology of the amino acid sequences of cellulose-binding domains is, the higher the probability of binding to the same site becomes, when the domains bind to a surface of cellulose or a shorter-chain β-1,4-glucan. Therefore, if the cellobiohydrolase and the β-glucosidase containing cellulose-binding domains with the amino acid sequences having a homology of not less than 70% are used, and when the cellobiohydrolase yields cellobiose, the probability of existence of the β-glucosidase in the same reaction field increases.

Consequently, with a saccharifying enzyme composition of the present invention, the endoglucanase, the cellobiohydrolase and the β-glucosidase can collaborate to carry out saccharification more efficiently.

While, if the homology is less than 70%, the cellobiohydrolase and the β-glucosidase may not be present sufficiently in the same reaction field.

In a saccharifying enzyme composition according to the present invention, the total content of the endoglucanase, the cellobiohydrolase and the β-glucosidase is preferably in the range of 30 to 80% by mass with respect to the total mass of the saccharifying enzyme composition.

If the total content of the endoglucanase, the cellobiohydrolase and the β-glucosidase is 80% by mass or higher with respect to the total mass of the saccharifying enzyme composition, the saccharification efficiency rather decreases, and therefore, it should better contain a hemicellulase such as a xylanase. If the total content of the endoglucanase, the cellobiohydrolase and the β-glucosidase is less than 30% by mass with respect to the total mass of the saccharifying enzyme composition, sufficient saccharification performance may not be attained.

Examples of the endoglucanase in a saccharifying enzyme composition according to the present invention may include that composed of the amino acid sequence according to SEQ ID NO:1. Examples of the cellobiohydrolase in a saccharifying enzyme composition according to the present invention may include that composed of the amino acid sequence according to SEQ ID NO:2. Examples of the β-glucosidase in a saccharifying enzyme composition according to the present invention may include that composed of the amino acid sequence according to SEQ ID NO:3.

A saccharifying enzyme composition according to the present invention preferably contains the endoglucanase, the cellobiohydrolase and the β-glucosidase at a mass ratio in the range of 0.2 to 2.5:1:0.2 to 2.5.

If the mass ratio of the endoglucanase to the mass of the cellobiohydrolase is less than 0.2, the production rate of a shorter-chain β-1,4-glucan produced from cellulose by the endoglucanase is too slow compared to the production rate of cellobiose produced from a shorter-chain β-1,4-glucan by the cellobiohydrolase, and sufficient saccharification efficiency may not be attained.

On the other hand, if the mass ratio of the endoglucanase to the cellobiohydrolase exceeds 2.5, the production rate of a shorter-chain β-1,4-glucan produced from cellulose by the endoglucanase is too high compared to the production rate of cellobioses produced from a shorter-chain β-1,4-glucan by the cellobiohydrolase, and sufficient saccharification efficiency may not be attained.

Meanwhile, if the mass ratio of the β-glucosidase to the cellobiohydrolase is less than 0.2, the production rate of glucose produced from cellobiose by the β-glucosidase is too slow compared to the production rate of cellobiose produced from a shorter-chain β-1,4-glucan by the cellobiohydrolase, and sufficient saccharification efficiency may not be attained.

On the other hand, if the mass ratio of the β-glucosidase to the cellobiohydrolase exceeds 2.5, the production rate of glucose produced from cellobiose by the β-glucosidase is too high compared to the production rate of cellobiose from a shorter-chain β-1,4-glucan by the cellobiohydrolase, and sufficient saccharification efficiency may not be attained.

A saccharifying enzyme composition according to the present invention may further contain a xylanase or a xylosidase. By containing a xylanase or a xylosidase, the saccharifying enzyme composition can saccharify hemicellulose contained in lignocellulose-based biomass as a substrate and yield xylose. Therefore, the composition can increase the saccharification rate of the lignocellulose-based biomass as a substrate.

A method for producing a saccharified solution according to the present invention is a method for producing a saccharified solution comprising adding a saccharifying enzyme to lignocellulose-based biomass as a substrate to form a substrate/saccharifying enzyme mixture, and then subjecting the substrate/saccharifying enzyme mixture to a saccharification treatment to yield a saccharified solution, wherein the method is characterized in that, as the saccharifying enzyme, at least an endoglucanase not containing a cellulose-binding domain, a cellobiohydrolase containing a cellulose-binding domain, and a β-glucosidase containing a cellulose-binding domain are added simultaneously to the substrate.

If enzymes are added simultaneously as above, first the endoglucanase acts on cellulose contained in lignocellulose-based biomass. Since the endoglucanase does not contain a cellulose-binding domain, when it is added to the substrate, it is not bound to a specific site of a surface of the cellulose and can contact non-specific sites over a wide range of a molecular chain of the cellulose to yield a shorter-chain β-1,4-glucan.

Since the cellobiohydrolase contains a cellulose-binding domain, it usually binds to cellulose and hydrolyzes the cellulose from its end to yield cellobiose, but if a shorter-chain β-1,4-glucan is present, it binds also to the shorter-chain β-1,4-glucan and hydrolyzes the same from its end to yield cellobiose. Therefore, if shorter-chain β-1,4-glucans are produced by the endoglucanase, the number of reaction initiation points for the cellobiohydrolase increases and the production of cellobioses by the cellobiohydrolase is promoted.

Further, since the β-glucosidase also contains a cellulose-binding domain, the β-glucosidase is also present in the reaction field where the cellobiohydrolase yields cellobiose. Consequently, the cellobiose yielded by the cellobiohydrolase is immediately hydrolyzed by the β-glucosidase to glucoses.

Since, according to a method for producing a saccharified solution according to the present invention, the endoglucanase, the cellobiohydrolase and the β-glucosidase collaborate to saccharify cellulose contained in lignocellulose-based biomass, a saccharified solution with a high sugar concentration can be efficiently yielded.

A method for producing a saccharified solution according to the present invention is a method for producing a saccharified solution comprising adding a saccharifying enzyme to lignocellulose-based biomass as a substrate to form a substrate/saccharifying enzyme mixture, and then subjecting the substrate/saccharifying enzyme mixture to a saccharification treatment to yield a saccharified solution, wherein the method is characterized in that, as the saccharifying enzyme, at least an endoglucanase not containing a cellulose-binding domain is added to the substrate, and thereafter at least a cellobiohydrolase containing a cellulose-binding domain, and a β-glucosidase containing a cellulose-binding domain are added.

If the endoglucanase is added previously as above, the cellobiohydrolase and β-glucosidase are not present in the reaction field of the endoglucanase. Therefore, the previously added endoglucanase can contact a molecular chain of cellulose more efficiently to hydrolyze preferentially cellulose contained in lignocellulose-based biomass to produce a shorter-chain β-1,4-glucan.

As the consequence, when the cellobiohydrolase and the β-glucosidase are added, compared to the case of simultaneous addition of the endoglucanase, the cellobiohydrolase and the β-glucosidase, the amount of a shorter-chain β-1,4-glucan has been increased. Therefore, the cellobiohydrolase can easily hydrolyze the shorter-chain β-1,4-glucan to cellobiose.

Since the β-glucosidase is present in the reaction field of hydrolysis by the cellobiohydrolase owing to the function of the cellulose-binding domain, it can hydrolyze efficiently the cellobiose to produce glucose.

Consequently, according to a method for producing a saccharified solution according to the present invention, by adding previously the endoglucanase and then adding the cellobiohydrolase and the β-glucosidase, a saccharified solution with a high sugar concentration can be yielded more efficiently.

BRIEF DESCRIPTION OF DRAWINGS

FIG. 1 is a flow chart showing an embodiment of a method for producing a saccharified solution according to the present invention.

DESCRIPTION OF EMBODIMENTS

Figure 2A:
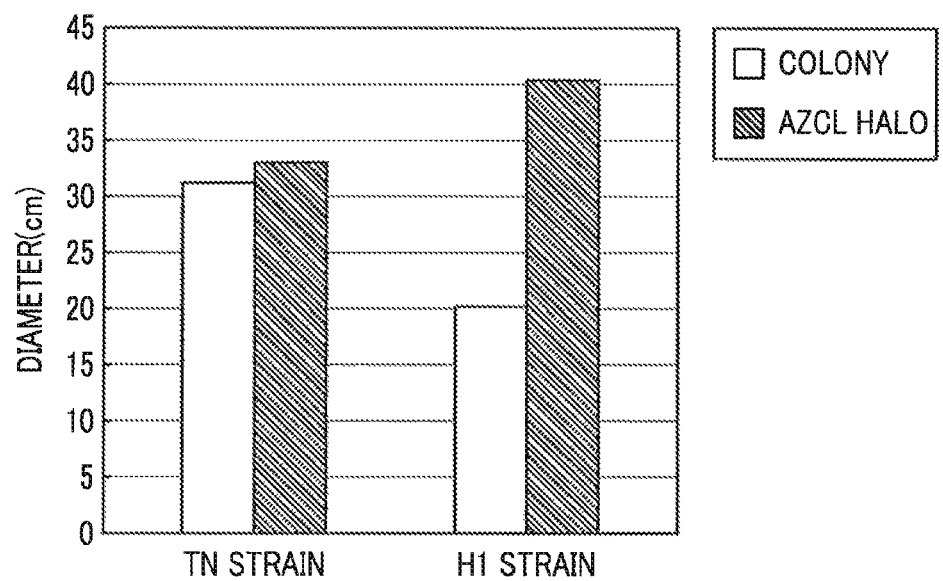
FIG. 2A and FIG. 2B are graphs showing the diameter of a colony of a strain, from which a saccharifying enzyme composition according to the present invention can be extracted and the diameter of an AZCL halo.

Embodiments of the present invention will be described below in more detail referring to the appended drawings.

FIG. 1 shows a process of saccharification treatments in producing ethanol using lignocellulose-based biomass as a substrate.

In the saccharification treatments, firstly ammonia water is mixed with rice straw roughly crushed as one of lignocellulose-based biomass as a substrate to prepare a substrate mixture containing rice straw and ammonia. In this case, the concentration of the ammonia water is in the range of 20 to 30% by mass/volume and the substrate mixture is regulated preferably to contain rice straw in the range of 20 to 70% by mass with respect to the ammonia water.

Then the prepared substrate mixture is retained at a temperature in the range of 25 to 100° C. for a time period in the range of 2 to 200 hours to carry out a pre-saccharification-treatment. As the result, an ammonia-containing pre-saccharification-treated product is yielded, in which lignin is dissociated from the rice straw as a substrate or the rice straw is swollen.

In this regard, the term "dissociate" means, in the present embodiment, at least a part of bonds in binding sites of lignin bound to cellulose, etc. is broken. The term "swell" means that, due to infiltration of a liquid, gaps are generated in cellulose, etc. constituting crystalline cellulose, or gaps are generated inside a cellulose fiber to expand.

Next, ammonia is separated by evaporating ammonia from the ammonia-containing pre-saccharification-treated product to yield an ammonia-separated pre-saccharification-treated product. Then the pH of the ammonia-separated pre-saccharification-treated product is adjusted to a range, in which saccharifying enzymes can work, for example in the range of pH 3 to 7.

Then saccharifying enzymes are added to the pH-adjusted ammonia-separated pre-saccharification-treated product to prepare a substrate/saccharifying enzyme mixture, and then a saccharification treatment is conducted by retaining the substrate/saccharifying enzyme mixture in the temperature range of 30 to 60° C. for 50 to 150 hours. By the saccharification treatment, cellulose contained in the substrate/saccharifying enzyme mixture is hydrolyzed by the action of the saccharifying enzymes. As the result, a saccharified solution containing a saccharide such as glucose can be yielded.

In a method for producing a saccharified solution according to the present embodiment, a saccharifying enzyme composition containing an endoglucanase not containing a cellulose-binding domain, a cellobiohydrolase containing a cellulose-binding domain, and a β-glucosidase containing a cellulose-binding domain are used as the saccharifying enzyme.

The endoglucanase, the cellobiohydrolase, and the β-glucosidase to be used in the present embodiment can be obtained, for example, by the following method.

Firstly, as a pre-mutation culture step, an *Acremonium cellulolyticus* TN strain (International Patent Microorganisms Depositary, The National Institute of Advanced Industrial Science and Technology; Accession number: FERM-BP-685; hereinafter abbreviated as "TN strain") is inoculated to a culture fluid having the composition shown in Table 1 and cultured overnight at 30° C. Then, as a mutagenic treatment step, the cultured TN strain is streaked on the surface of a solid culture medium having the composition shown in Table 2 and irradiated with ultraviolet light to obtain a mutagenically treated strain. Subsequently, the mutagenically treated strain is cultured at 30° C. for 7 days as a post-mutation culture step.

TABLE 1

| Composition | Concentration (% by mass/volume) |
|---|---|
| Rice straw | 5.0 |
| $KH_2PO_4$ | 0.2 |
| $(NH_4)_2SO_4$ | 0.14 |
| Urea | 0.4 |
| Polyoxyethylene sorbitan monooleate | 0.1 |
| $MgSO_4 \cdot 7H_2O$ | 0.03 |
| $ZnSO_4 \cdot 7H_2O$ | 0.007 |
| $MnSO_4 \cdot 6H_2O$ | 0.001 |
| $CuSO_4 \cdot 7H_2O$ | 0.005 |

TABLE 2

| Composition | Concentration (% by mass/volume) |
|---|---|
| Rice straw | 1.0 |
| AZCL-He-Cellulose | 0.02 |
| Acetate buffer solution (pH 4) | 20 (mM) |
| Agar | 2.0 |

AZCL-HE-CELLULOSE (trade name, by Megazyme International Ireland) contained in the solid culture medium as a color developing substrate is a substance, which develops a blue color when degraded by a saccharifying enzyme. Therefore, when the mutagenically treated strain produces a saccharifying enzyme by the culture, the AZCL-HE-CELLULOSE is degraded by the saccharifying enzyme, and a blue circle (hereinafter referred to as "AZCL halo") having a size corresponding to the amount of the saccharifying enzyme produced is formed around a colony of the mutagenically treated strain.

Then a colony with the maximum size of the AZCL halo is selected as an inoculum, and the pre-mutation culture step, the mutagenic treatment step and the post-mutation culture step are repeated again. From the resulting colonies, several colonies are selected according to the sizes thereof and the sizes of the AZCL halos formed therearound.

Each strain of the selected colonies and the TN strain was inoculated on a new medium of the solid culture medium and cultured at 30° C. for 7 days. The diameters of colonies and the diameters of AZCL halos were measured and (diameter of AZCL halo)/(diameter of colony) was calculated.

Further, each strain of the selected colonies and the TN strain was inoculated in a new medium of the culture fluid and cultured at 30° C., then a culture under the conditions of pH 5.5 and 30° C. was started. On days 7, 10, 11, 12, 13, 14, and 17, the carboxymethylcellulose (CMC) degradation activity was measured. The CMC degradation activity was measured as follows.

Firstly, to 10 μL of an aqueous solution sample containing a saccharifying enzyme, 190 μL of a 200 mM acetate buffer solution (pH 5.5) and 200 μL of an 1% by mass/volume aqueous solution of CMC (Grade No. 1.02331.0500, by Merck & Co., Inc.) are added and reacted at 30° C. for 15 min.

Then to the reacted solution, 400 μL of an aqueous solution containing 30% by mass/volume of Rochelle salt, 1% by mass/volume of dinitrosalicylic acid, and 1.6% by mass/volume of sodium hydroxide is added and treated at 100° C. for 5 min. Next, the absorbance of the light of a wavelength of 540 nm for the obtained solution is measured and the concentration of an eluted reducing sugar is calculated based on a standard substance of glucose. In this regard, the enzyme quantity which liberates 1 μmol of reducing sugar per min is defined as 1 U.

Out of the selected colonies, the one having the highest value of (diameter of AZCL halo)/(diameter of colony) and CMC degradation activity calculated as above is selected as the *Acremonium cellulolyticus* H1 strain (International Patent Microorganisms Depositary, The National Institute of Advanced Industrial Science and Technology; Accession number: FERM-P-22164; hereinafter abbreviated as "H1 strain") and used as a strain used for extraction of a saccharifying enzyme composition of the present embodiment.

Figure 2B:
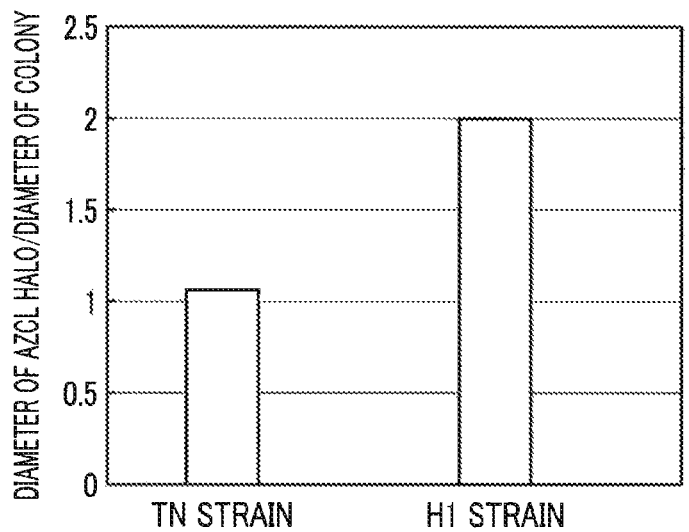

In FIGS. 2A and 2B are shown the colony diameters, the AZCL halo diameters, and the values of (diameter of AZCL halo)/(diameter of colony) with respect to the H1 strain and the TN strain. The CMC degradation activity values of the H1 strain and the TN strain is shown in FIG. 3.

As obvious from FIG. 2A, the AZCL halo diameter with respect to the colony of the H1 strain is larger compared to the colony of the TN strain. Therefore, it is clear that the H1 strain produces more saccharifying enzyme than the TN strain.

Further, as obvious from FIG. 2B, with respect to the colony of the H1 strain, the value of (diameter of AZCL halo)/(diameter of colony) is about twice as large as the colony of the TN strain. Therefore, it is clear that the H1 strain has higher saccharifying enzyme activity per fungus body compared to the TN strain.

Figure 3:
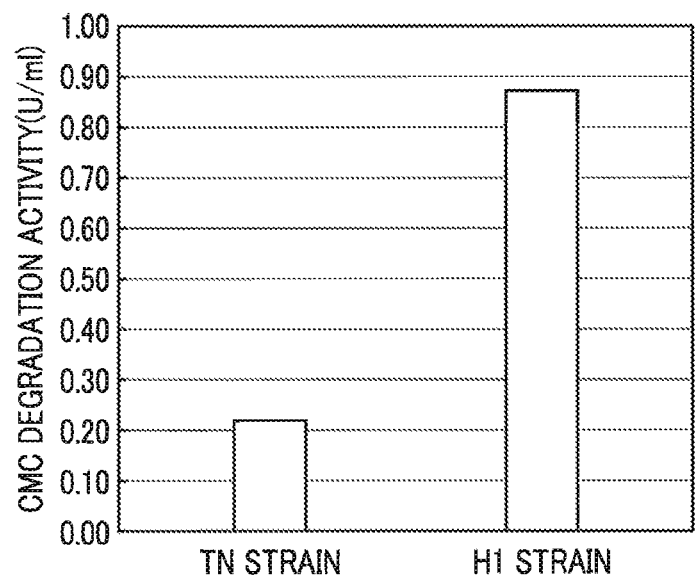
FIG. 3 is a graph showing the CMC degradation activity of a strain, from which a saccharifying enzyme composition according to the present invention can be extracted.

From FIG. 3, it is obvious that the H1 strain has significantly higher CMC degradation activity compared to the TN strain. Since the CMC degradation activity is used as an indicator representing the cellulose degradation activity, it is clear that the H1 strain produces a saccharifying enzyme superior to that of the TN strain.

Next, a method for extracting saccharifying enzymes used in the present embodiment, namely, an endoglucanase, a cellobiohydrolase, and a β?glucosidase, from the H1 strain will be described.

Firstly, the H1 strain is inoculated in a culture fluid having the composition shown in Table 3 and cultured at 30° C. for 14 days. The culture fluid in which the strain has been cultured is filtrated with a filter having a pore size of 0.2 μm.

TABLE 3

| Composition | Concentration (% by mass/volume) |
|---|---|
| Ammonia-separated pre-saccharification-treated product | 5.0 |
| $(NH_4)_2SO_4$ | 0.5 |
| Urea | 0.4 |
| $KH_2PO_4$ | 2.4 |
| $MgSO_4 \cdot 7H_2O$ | 0.12 |
| $ZnSO_4 \cdot 7H_2O$ | 0.001 |
| $MnSO_4 \cdot 6H_2O$ | 0.001 |
| $CuSO_4 \cdot 7H_2O$ | 0.001 |
| Polyoxyethylene sorbitan monooleate | 0.1 |

The obtained filtrate is separated by the 1st separation column (trade name: Bio-Rad Econo-Column, diameter 5.0 cm×length 50.0 cm; by Bio-Rad Laboratories, Inc.) filled with an anion exchange medium (trade name: TOYOPEARL QAE-550C; by Tosoh Corporation) to obtain fractions Q1 to Q12 according to the elution time.

Next, the obtained fraction Q1 is heat-treated at 50° C. for 24 hours, then centrifuged (9460×g, 20 min), and the obtained supernatant is filtrated with a filter having a pore size of 0.2 μm. The obtained filtrate is separated by the 2nd separation column (trade name: Mono S 5.50L column; by GE Healthcare Japan) to obtain fractions S1 to S9 according to the elution time. An endoglucanase not containing a cellulose-binding domain is obtained from the fraction S3. The endoglucanase is a saccharifying enzyme composed of the amino acid sequence according to SEQ ID NO:1.

Next, the fraction Q3 is separated by the 3rd separation column (trade name: XK26/20 column; diameter 2.6 cm×length 20 cm; by GE Healthcare Japan) filled with a hydrophobic medium (trade name: TOYOPEARL Butyl-650M; by Tosoh Corporation) to obtain fractions B1 to B8 according to the elution time.

Then, a cellobiohydrolase containing a cellulose-binding domain is obtained from the fraction B7. The cellobiohydrolase is a saccharifying enzyme composed of the amino acid sequence according to SEQ ID NO:2. Further, a β-glucosidase containing a cellulose-binding domain is obtained from the fraction B8. The β-glucosidase is a saccharifying enzyme composed of the amino acid sequence according to SEQ ID NO:3.

A homology search of the amino acid sequences of the endoglucanase, the cellobiohydrolase and the β-glucosidase thus obtained was conducted with respect to cellulose-binding domains using the Pfam database as a motif library.

As the result, it has come to be known that, with respect to the cellobiohydrolase, amino acid sequences 497 to 529 in the amino acid sequence according to SEQ ID NO:2 is a cellulose-binding domain. Similarly, it has come to be known that, with respect to the β-glucosidase, amino acid sequences 780 to 812 in the amino acid sequence according to SEQ ID NO: 3 is a cellulose-binding domain. It has come to be known that the endoglucanase does not contain a cellulose-binding domain.

Next, homology assessment was conducted on the amino acid sequences of cellulose-binding domains of the cellobiohydrolase and the β-glucosidase, for example, using BLAST searches at the site of NCBI (National Center for Biotechnology Information) to find a homology of 24/33, namely 72.7%.

Cellulose-binding domains with amino acid sequences having higher homology bind to the same site with the higher probability, when they bind to a surface of cellulose or a shorter-chain β-1,4-glucan. Therefore, by using the cellobiohydrolase and the β-glucosidase containing cellulose-binding domains with the amino acid sequences having a homology of 72.7%, the probability of presence of the β-glucosidase in the same reaction field when the cellobiohydrolase generates cellobiose becomes high.

Consequently, with a saccharifying enzyme composition of the present embodiment, the endoglucanase, the cellobiohydrolase, and the β-glucosidase can collaborate for more efficient saccharification.

For a saccharifying enzyme composition of the present embodiment, the total content of the endoglucanase, the cellobiohydrolase and the β-glucosidase to be obtained as above is selected in the range of 30 to 80% by mass with respect to the total mass of the saccharifying enzyme composition. Further, a saccharifying enzyme composition containing the endoglucanase, the cellobiohydrolase and the β-glucosidase to be obtained as above at a mass ratio in the range of 0.2 to 2.5:1:0.2 to 2.5 is used in the present embodiment.

By a method for producing a saccharified solution according to the present embodiment, the endoglucanase, the cellobiohydrolase, and the β-glucosidase constituting the saccharifying enzyme composition are added simultaneously to the pH-adjusted ammonia-separated pre-saccharification-treated product.

By doing so, the endoglucanase, the cellobiohydrolase, and the β-glucosidase collaborate to saccharify cellulose contained in lignocellulose-based biomass, and consequently can efficiently yield a saccharified solution with a high concentration of a saccharide such as glucose.

Although, in the present embodiment, the endoglucanase, the cellobiohydrolase, and the β-glucosidase constituting the saccharifying enzyme composition are added simultaneously to the pH-adjusted ammonia-separated pre-saccharification-treated product, the endoglucanase may be added alone previously to the pH-adjusted ammonia-separated pre-saccharification-treated product to carry out an enzymatic saccharification treatment for a predetermined time period, and thereafter the cellobiohydrolase and the β-glucosidase may be added.

According to a method for producing a saccharified solution according to the present invention, by adding firstly the endoglucanase, and then adding the cellobiohydrolase and the β-glucosidase, a saccharified solution with a high sugar concentration can be yielded more efficiently.

Although, in the present embodiment, the saccharifying enzyme composition containing only the endoglucanase not containing the cellulose-binding domain, the cellobiohydrolase containing the cellulose-binding domain, and the β-glucosidase containing the cellulose-binding domain is used, the saccharifying enzyme composition may further contain a xylanase or a xylosidase.

By containing a xylanase or a xylosidase, hemicellulose contained in lignocellulose-based biomass can be enzymatically saccharified to xylose, and therefore the saccharification rate of the lignocellulose-based biomass can be improved.

Next, Examples and Comparative Examples of the present invention will be described.

EXAMPLE

Example 1

In this Example, firstly rice straw was finely milled as lignocellulose-based biomass as a substrate, to which 25% by mass ammonia water was added to a mass ratio of 1:2.5 to yield a substrate mixture containing rice straw and ammonia. Next, the substrate mixture was retained at a temperature of 80° C. for 8 hours to perform a pre-saccharification treatment, then ammonia was separated and the pH was adjusted to 4.0. The content of rice straw was adjusted to 20% by volume to obtain a pre-saccharification-treated product of this Example.

A saccharifying enzyme composition was prepared by mixing an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase (endo-1,4-beta-xylanase A originated from *Thermoascus aurantiacus*; GenBank ACCESSION No. AAF24127) and a β-xylosidase (β-xylosidase originated from *Thermotoga maritima*; by Thermostable Enzyme Laboratory Co., Ltd.) at a mass ratio of 0.3:1:0.3:1.0:0.7. The composition was added to the pretreated product to a final concentration of 2 mg per g of rice straw, and the mixture was subjected to a saccharification treatment at 50° C. for 72 hours to obtain a saccharification-treated product. Although, in this case, a xylanase and a β-xylosidase originated from specific fungi were used, any enzymes, which have endoxylanase activity and β-xylosidase activity, may be used. Then the saccharified solution was heat-treated at 95° C. for 5 min, centrifuged at 15,760×g, 4° C. for 5 min, and the supernatant was transferred to a new 1.5 mL Eppendorf tube. After filtration with a filter having a pore size of 0.2 μm, the sugar concentration was measured by an HPLC.

Figure 4:
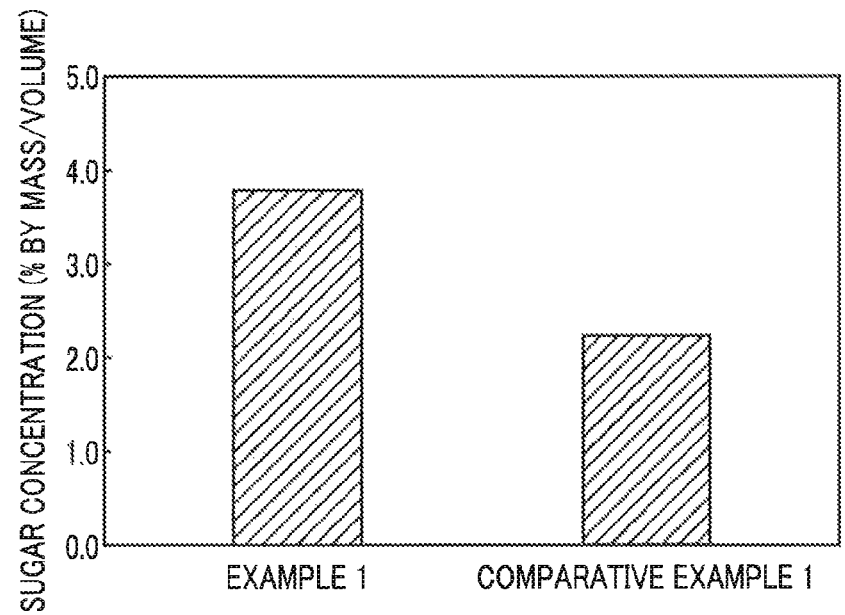
FIG. 4 is a graph showing the saccharification performance of a saccharifying enzyme according to the present invention.

The sugar concentration was measured by the HPLC with a separator (trade name: Waters 2695; by Nihon Waters K. K.), an RI detector (trade name: Waters 2414; by Nihon Waters K. K.), and a separation column (trade name: HPX-87P column; by Bio-Rad Laboratories, Inc.) under conditions of the column temperature at 85° C., and the detector temperature at 40° C. using ultrapure water as an eluent at a flow rate of 0.6 mL/min. The results are shown in FIG. 4. In FIG. 4, the total of glucose and xylose is shown as the sugar concentration.

Comparative Example 1

In this Comparative Example, a saccharified solution was produced, exactly as in Example 1, except that a commercially available saccharifying enzyme (trade name: *Acremonium* cellulase; by Meiji Seika Pharma Co., Ltd.) was used; and the glucose concentration of the saccharified solution was measured. The results are shown in FIG. 4.

As shown in FIG. 4, the sugar concentration of the saccharified solution of the Example produced using a saccharifying enzyme composition composed of the endoglucanase, the cellobiohydrolase, and the β-glucosidase was 3.8% by mass/volume, and the sugar concentration of the saccharified solution of the Comparative Example produced using the *Acremonium* cellulase (trade name) was 2.3% by mass/volume.

Consequently, by the saccharifying enzyme composition of the Example, the sugar concentration of a saccharified solution yielded by an enzymatic saccharification treatment for a predetermined time period can be clearly increased approximately 1.7-fold compared to the saccharifying enzyme of the Comparative Example. In other words, the saccharifying enzyme composition of the Example in an amount 1.7-fold less than the amount of the saccharifying enzyme of the Comparative Example can yield a saccharified solution with the equivalent sugar concentration, demonstrating clearly good saccharification performance with a low usage thereof Example 2

Next, the total content of enzymes according to the present invention was investigated.

Example 2-1

Figure 5:
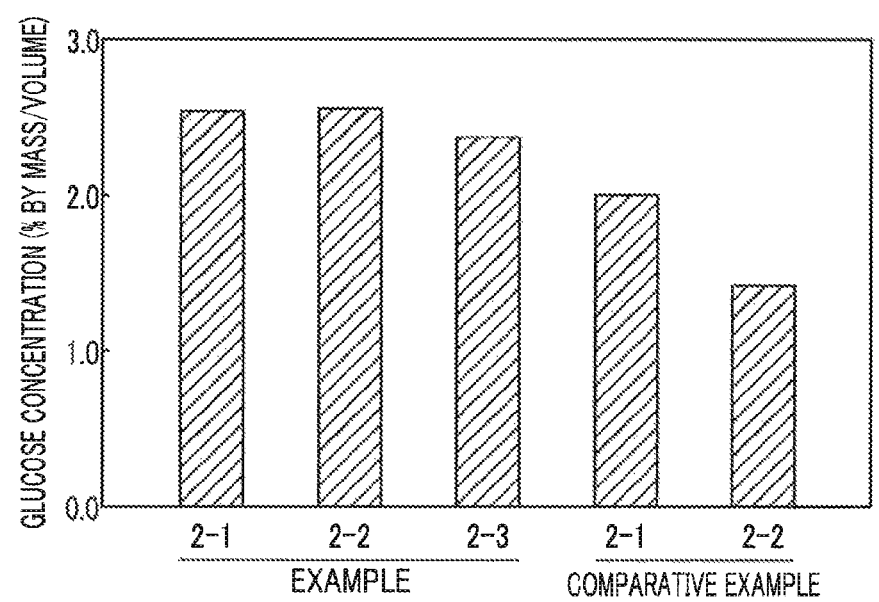
FIG. 5 is a graph showing the results of investigations about the influence of the content with respect to the total mass of a saccharifying enzyme composition according to the present invention on the production of glucose.

In this Example, a saccharification treatment was conducted exactly the same as Example 1, except that a saccharifying enzyme composition was prepared by mixing an endoglucanase composed of the amino acid sequence according to SEQ ID NO:1, a cellobiohydrolase composed of the amino acid sequence according to SEQ ID NO:2, and a β-glucosidase composed of the amino acid sequence according to SEQ ID NO:3 at a mass ratio of 0.3:1:0.3 to constitute 35.1% of the total enzyme mass, to yield a saccharification treatment product, whose glucose concentration was measured. The results are shown in FIG. 5.

Example 2-2

In this Example, a saccharification treatment was conducted exactly the same as Example 2-1, except that a saccharifying enzyme composition was prepared such that an endoglucanase composed of the amino acid sequence according to SEQ ID NO:1, a cellobiohydrolase composed of the amino acid sequence according to SEQ ID NO:2, and a β-glucosidase composed of the amino acid sequence according to SEQ ID NO:3 constituted 56.7% of the total enzyme mass, to yield a saccharification treatment product, whose glucose concentration was measured. The results are shown in FIG. 5.

Example 2-3

In this Example, a saccharification treatment was conducted exactly the same as Example 2-1, except that a saccharifying enzyme composition was prepared such that an endoglucanase composed of the amino acid sequence according to SEQ ID NO:1, a cellobiohydrolase composed of the amino acid sequence according to SEQ ID NO:2, and a β-glucosidase composed of the amino acid sequence according to SEQ ID NO:3 constituted 78.4% of the total enzyme mass, to yield a saccharification treatment product, whose glucose concentration was measured. The results are shown in FIG. 5.

Comparative Example 2-1

In this Comparative Example, a saccharification treatment was conducted exactly the same as Example 2-1, except that a saccharifying enzyme composition was prepared such that an endoglucanase composed of the amino acid sequence according to SEQ ID NO:1, a cellobiohydrolase composed of the amino acid sequence according to SEQ ID NO:2, and a β-glucosidase composed of the amino acid sequence according to SEQ ID NO:3 constituted 13.5% of the total enzyme mass, to yield a saccharification treatment product, whose glucose concentration was measured. The results are shown in FIG. 5.

Comparative Example 2-2

In this Comparative Example, a saccharification treatment was conducted exactly the same as Example 2-1, except that a saccharifying enzyme composition was prepared such that an endoglucanase composed of the amino acid sequence according to SEQ ID NO:1, a cellobiohydrolase composed of the amino acid sequence according to SEQ ID NO:2, and a β-glucosidase composed of the amino acid sequence according to SEQ ID NO:3 constituted 100% of the total enzyme mass, to yield a saccharification treatment product, whose glucose concentration was measured. The results are shown in FIG. 5.

As shown in Comparative Example 2-1 in FIG. 5, if the percentage of the content of an endoglucanase, a cellobiohydrolase, and a β-glucosidase of the present invention is as low as 13.5% with respect to the total enzyme mass, the glucose concentration of a saccharification treatment product becomes also as low as 2.0%. This is conceivably because the saccharification efficiency is low due to a low enzyme concentration.

It does not mean that the higher the total content of an endoglucanase, a cellobiohydrolase, and a β-glucosidase of the present invention is, the better it is. As seen from Comparative Example 2-2, if the saccharifying enzyme composition is adjusted to 100% of the total enzyme mass, the glucose concentration of a saccharification treatment product rather decreases to 1.5%.

Lignocellulose-based biomass is constituted of cellulose and hemicellulose, which exists covering cellulose surfaces. It is believed that, if a hemicellulase is present, hemicellulose degradation advances and saccharification progresses more efficiently, and the sugar concentration of a saccharification treatment product increase in a short time period. Consequently, with the presence of a hemicellulase such as a xylanase in addition to an endoglucanase, a cellobiohydrolase, and a β-glucosidase, a saccharification treatment can be performed more efficiently.

Therefore, the total content of an endoglucanase, a cellobiohydrolase, and a β-glucosidase of the present invention is preferably in the range of 30 to 80% by mass. If the total content of the enzymes is within the range, the efficiency is high and the glucose concentration of a saccharification treatment product is not less than about 2.4%.

Example 3

Next, the mass ratio among enzymes in a saccharifying enzyme composition was investigated.

Example 3-1

Figure 6:
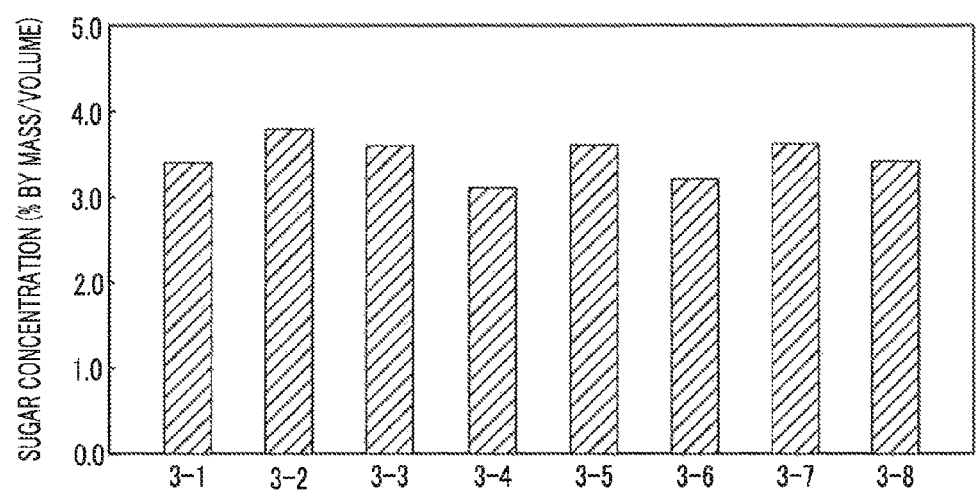
FIG. 6 is a graph showing the results of investigation about the influence of the mass ratio of an endoglucanase, a cellobiohydrolase, a β-glucosidase, a xylanase, and a β-xylosidase in a saccharifying enzyme composition according to the present invention on the production of a saccharide.

A saccharifying enzyme composition was prepared by mixing an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase at a mass ratio of 0.2:1:0.2:0.2:0.2. The composition was added to the pretreated product to a final concentration of 2 mg per g of rice straw, and the mixture was subjected to a saccharification treatment at 50° C. for 72 hours to obtain a saccharification-treated product. Adjustment of a saccharified solution, and measurement of a sugar concentration were carried out as in Example 1. The mixing ratio among the respective enzymes is shown in Table 4, and the results are shown in FIG. 6.

Example 3-2

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 0.3:1:0.3:1.0:0.7. The mixing ratio among the respective enzymes is shown in Table 4, and the results are shown in FIG. 6.

Example 3-3

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 0.3:1:1.0:0.7:0.3. The mixing ratio among the respective enzymes is shown in Table 4, and the results are shown in FIG. 6.

Example 3-4

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 0.5:1:2.5:0.5:0.5. The mixing ratio among the respective enzymes is shown in Table 4, and the results are shown in FIG. 6.

Example 3-5

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 1.0:1:0.3:0.7:0.3. The mixing ratio among the respective enzymes is shown in Table 4, and the results are shown in FIG. 6.

Example 3-6

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 2.5:1:0.5:0.5:0.5. The mixing ratio among the respective enzymes is shown in Table 4, and the results are shown in FIG. 6.

Example 3-7

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 0.3:1:0.3:

1.3:0.3. The mixing ratio among the respective enzymes is shown in Table 4, and the results are shown in FIG. 6.

Example 3-8

Measurement of a sugar concentration was carried out as in Example 1 except that an endoglucanase composed of the amino acid sequence according to SEQ ID NO:1, a cellobiohydrolase composed of the amino acid sequence according to SEQ ID NO:2, a β-glucosidase composed of the amino acid sequence according to SEQ ID NO:3, a xylanase and a β-xylosidase were mixed at a mass ratio of 0.3:1:0.3:0.3:1.3. The mixing ratio among the respective enzymes is shown in Table 4, and the results are shown in FIG. 6.

TABLE 4

|  | Endoglucanase | Cellobiohydrolase | β-glucosidase | Xylanase | β-xylosidase |
| --- | --- | --- | --- | --- | --- |
| Example 3-1 | 0.2 | 1.0 | 0.2 | 0.2 | 0.2 |
| Example 3-2 | 0.3 | 1.0 | 0.3 | 1.0 | 0.7 |
| Example 3-3 | 0.3 | 1.0 | 1.0 | 0.7 | 0.3 |
| Example 3-4 | 0.5 | 1.0 | 2.5 | 0.5 | 0.5 |

TABLE 4-continued

|  | Endoglucanase | Cellobiohydrolase | β-glucosidase | Xylanase | β-xylosidase |
| --- | --- | --- | --- | --- | --- |
| Example 3-5 | 1.0 | 1.0 | 0.3 | 0.7 | 0.3 |
| Example 3-6 | 2.5 | 1.0 | 0.5 | 0.5 | 0.5 |
| Example 3-7 | 0.3 | 1.0 | 0.3 | 1.3 | 0.3 |
| Example 3-8 | 0.3 | 1.0 | 0.3 | 0.3 | 1.3 |

As shown in FIG. 6, if an endoglucanase, a cellobiohydrolase, and a β-glucosidase of the present invention are mixed at a mass ratio in the range of 0.2 to 2.5:1:0.2 to 2.5, a saccharification reaction can be performed very efficiently leading always to a final sugar concentration of 3.0% or higher.

The addition amount of a xylanase or a xylosidase is preferably 0.2 to 1.3 with respect to the mass ratio 1 of a cellobiohydrolase.

An enzyme composition that can saccharify a substrate very efficiently despite a small amount of enzymes can now be provided according to the present invention, by using plural enzymes considering their binding to a substrate, and investigating in detail the mass ratio among them.

The invention claimed is:

1. A saccharifying enzyme composition for subjecting lignocellulose-based biomass as a substrate to a saccharification treatment, the composition comprising a mixture of:
    an endoglucanase not containing a cellulose-binding domain as set forth in SEQ ID NO:1;
    a cellobiohydrolase containing a cellulose-binding domain as set forth in SEQ ID NO:2; and
    a β-glucosidase containing a cellulose-binding domain as set forth in SEQ ID NO:3;
    wherein the endoglucanase, the cellobiohydrolase and the β-glucosidase collectively account for 30% to 80% by mass of all enzymes present in the saccharifying enzyme composition, and
    wherein the endoglucanase, the cellobiohydrolase and the β-glucosidase are present in the saccharifying enzyme composition in a mass ratio in a range of 0.2 to 2.5:1:0.2 to 2.5.

2. The saccharifying enzyme composition of claim 1, further comprising one or both of a xylanase and a xylosidase.

3. The saccharifying enzyme composition of claim 1;
    wherein the endoglucanase, the cellobiohydrolase and the β-glucosidase are obtained from an *Acremonium cellulolyticus* H1 strain having cellulose assimilating ability.

4. The saccharifying enzyme composition of claim 1;
    wherein the endoglucanase, the cellobiohydrolase, and the β-glucosidase are produced by culturing an *Acremonium cellulolyticus* H1 strain.

* * * * *

SEQUENCE LISTING

<160> NUMBER OF SEQ ID NOS: 3

<210> SEQ ID NO 1
<211> LENGTH: 226
<212> TYPE: PRT
<213> ORGANISM: Acremonium cellulolyticus

<400> SEQUENCE: 1

```
Met Lys Leu Thr Phe Leu Leu Asn Leu Ala Val Ala Ala Ser Ala Gln
1               5                   10                  15

Gln Ser Leu Cys Ser Gln Tyr Ser Ser Tyr Thr Ser Gly Gln Tyr Ser
            20                  25                  30

Val Asn Asn Leu Trp Gly Glu Ser Ser Gly Ser Gly Ser Gln Cys
            35                  40                  45

Thr Tyr Val Asn Ser Ile Ser Ser Ser Gly Val Ser Trp Ser Thr Thr
    50                  55                  60

Trp Asn Trp Ser Gly Gly Ser Thr Ser Val Lys Ser Tyr Ala Asn Ser
65                  70                  75                  80

Gln Leu Ser Gly Leu Thr Lys Lys Leu Val Ser Asn Leu Gln Ser Ile
                85                  90                  95

Pro Thr Ser Val Gln Trp Ser Tyr Ser Asn Thr Asn Ile Val Ala Asp
            100                 105                 110

Val Ser Tyr Asp Leu Phe Thr Ala Ala Asp Ile Asn His Val Thr Tyr
        115                 120                 125

Ser Gly Asp Tyr Glu Leu Met Ile Trp Leu Gly Lys Tyr Gly Gly Ala
    130                 135                 140

Gln Pro Leu Gly Ser Gln Ile Gly Thr Ala Asn Val Gly Gly Ala Thr
145                 150                 155                 160

Trp Gln Leu Trp Tyr Gly Val Asn Gly Ser Gln Lys Thr Tyr Ser Phe
                165                 170                 175

Val Ala Ser Ser Gln Thr Thr Ser Trp Asn Gly Asp Ile Leu Gln Phe
            180                 185                 190

Phe Lys Tyr Leu Gln Ser Asn Gln Gly Phe Pro Ala Ser Ser Gln Tyr
        195                 200                 205
```

Leu Ile Asp Leu Gln Phe Gly Thr Glu Pro Phe Thr Gly Ser Gln Thr
            210                 215                 220

Thr Leu
225

<210> SEQ ID NO 2
<211> LENGTH: 529
<212> TYPE: PRT
<213> ORGANISM: Acremonium cellulolyticus

<400> SEQUENCE: 2

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Phe Thr Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn

```
            340                 345                 350
Val Ile Asn Ser Asp Tyr Cys Ala Ala Glu Ile Ser Thr Phe Gly Gly
            355                 360                 365

Thr Ala Ser Phe Ser Lys His Gly Gly Leu Thr Asn Met Ala Ala Gly
        370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ala Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Thr Thr Thr Thr Ala Ser Arg Thr Thr Thr Thr Ser Ala
465                 470                 475                 480

Ser Ser Thr Ser Thr Ser Ser Thr Ser Thr Gly Thr Gly Val Ala Gly
                485                 490                 495

His Trp Gly Gln Cys Gly Gly Gln Gly Trp Thr Gly Pro Thr Thr Cys
            500                 505                 510

Val Ser Gly Thr Thr Cys Thr Val Val Asn Pro Tyr Tyr Ser Gln Cys
        515                 520                 525

Leu

<210> SEQ ID NO 3
<211> LENGTH: 813
<212> TYPE: PRT
<213> ORGANISM: Acremonium cellulolyticus

<400> SEQUENCE: 3

Met Tyr Ser Ala Phe Leu Leu Leu Ala Ser Ala Thr Pro Ile Val
1               5                   10                  15

Ser Ala Gln Ser Ala Ser Trp Ser Ala Ala Tyr Ser Lys Ala Thr Ala
                20                  25                  30

Ala Leu Ser Lys Leu Ser Gln Asn Asp Lys Ile Gly Met Val Thr Gly
            35                  40                  45

Val Gly Trp Gly Lys Gly Pro Cys Val Gly Asn Thr Ala Ala Pro Ser
        50                  55                  60

Gly Ile Ser Phe Pro Ser Leu Cys Ile Gln Asp Ser Pro Leu Gly Val
65                  70                  75                  80

Arg Tyr Ala Asn Pro Val Thr Ala Phe Pro Ala Gly Thr Asn Ala Gly
                85                  90                  95

Met Thr Trp Asp Arg Thr Leu Met Asn Gln Arg Gly Ala Ala Leu Gly
            100                 105                 110

Ala Glu Ser Lys Gly Leu Gly Val His Val Gln Leu Gly Pro Val Ala
        115                 120                 125

Gly Pro Leu Gly Lys Ile Ala Gln Gly Gly Arg Gly Trp Glu Gly Phe
    130                 135                 140

Gly Thr Asp Pro Tyr Leu Ser Gly Val Ala Met Ile Glu Thr Ile Ser
145                 150                 155                 160

Gly Met Gln Ser Ser Gly Thr Gln Ala Cys Ala Lys His Tyr Ile Gly
                165                 170                 175

Asn Glu Gln Glu Leu Asn Arg Glu Ser Met Ser Ser Asn Ile Asp Asp
```

-continued

```
                180                 185                 190
Arg Thr Leu His Glu Leu Tyr Leu Trp Pro Phe Ala Asp Ala Val Arg
            195                 200                 205
Ala Asn Val Ala Ser Val Met Cys Ser Tyr Asn Gln Ile Asn Gly Thr
        210                 215                 220
Phe Ser Cys Glu Asn Glu Ser Met Thr Gly Ile Leu Lys Thr Glu
225                 230                 235                 240
Leu Gly Phe Pro Gly Tyr Ile Met Ser Asp Trp Asp Ala Gln His Thr
                245                 250                 255
Thr Val Thr Ser Ala Asn Ser Gly Leu Asp Met Thr Met Pro Gly Ser
            260                 265                 270
Asp Tyr Ser Asp Thr Pro Ser Ser Val Leu Trp Gly Gln Asn Leu Ala
        275                 280                 285
Asn Ala Ile Ser Ser Gly Gln Val Ala Gln Ser Arg Leu Asp Asp Met
        290                 295                 300
Val Thr Arg Ile Leu Ala Ala Trp Tyr Leu Val Gly Gln Asp Gln Gly
305                 310                 315                 320
Phe Pro Ala Val Ala Phe Asn Ser Trp Thr Gly Gly Gln Ala Ser Val
                325                 330                 335
Asn Val Thr Ser Asn His Asn Gln Val Ala Arg Ala Val Ala Arg Asp
            340                 345                 350
Ser Ile Val Leu Leu Lys Asn Thr Asn Ser Thr Leu Pro Leu Asn Lys
        355                 360                 365
Pro Ser Ser Ile Ala Ile Ile Gly Thr Asp Ala Gln Thr Asn Pro Ser
        370                 375                 380
Gly Pro Asn Ala Cys Thr Asp Arg Gly Cys Asp Thr Gly Thr Leu Ala
385                 390                 395                 400
Met Gly Trp Gly Ser Gly Thr Cys Gln Phe Pro Tyr Leu Thr Asp Pro
                405                 410                 415
Leu Thr Ala Ile Lys Thr Arg Ala Ala Ser Asp Gly Thr Thr Ile Thr
            420                 425                 430
Thr Ser Ile Ser Asp Asn Gly Ser Ala Gly Ala Ser Val Ala Gln Ser
        435                 440                 445
Ala Glu Tyr Ala Ile Val Phe Ile Asn Ser Asp Ser Gly Glu Gly Tyr
        450                 455                 460
Ile Thr Val Glu Gly Val Ala Gly Asp Arg Asn Asn Leu Asp Pro Trp
465                 470                 475                 480
His Ser Gly Asn Ala Leu Val Gln Ser Val Ala Ala Val Asn Lys Lys
                485                 490                 495
Thr Ile Val Val Ile His Ser Val Gly Pro Val Ile Leu Glu Thr Ile
            500                 505                 510
Leu Ala Gln Pro Asn Val Val Ala Val Trp Ala Gly Ile Pro Gly
        515                 520                 525
Gln Glu Ser Gly Ser Ala Leu Thr Asp Ile Leu Tyr Gly Ser Thr Ala
        530                 535                 540
Pro Ser Gly Lys Leu Thr Tyr Thr Ile Ala Lys Gln Ala Ser Asp Tyr
545                 550                 555                 560
Gly Thr Ala Val Val Ser Gly Ser Asp Asn Tyr Pro Glu Gly Leu Phe
                565                 570                 575
Ile Asp Tyr Arg His Phe Asp Lys Ser Asn Ile Glu Pro Arg Tyr Glu
            580                 585                 590
Phe Gly Tyr Gly Leu Ser Tyr Thr Thr Phe Gly Tyr Thr Asn Leu Ala
        595                 600                 605
```

```
Ile Asp Ile Thr Val Ser Thr Gly Pro Thr Thr Gly Gln Ile Val Pro
    610             615             620
Gly Gly Pro Ser Asp Leu Phe Glu Ser Val Gly Thr Val Thr Val Gln
625             630             635                         640
Val Ala Asn Thr Gly Ser Val Ala Gly Ser Glu Val Ala Gln Leu Tyr
            645             650             655
Ile Gly Leu Pro Ser Ser Ala Pro Ser Ser Pro Pro Lys Gln Leu Arg
            660             665             670
Gly Phe Asp Lys Leu Ser Leu Ala Ala Gly Ala Ser Gly Thr Ala Thr
        675             680             685
Phe Asp Leu Thr Arg Arg Asp Leu Ser Tyr Trp Asp Val Ser Lys Gln
    690             695             700
Lys Trp Val Val Pro Ser Gly Ala Phe Thr Val Tyr Val Gly Ala Ser
705             710             715                         720
Ser Arg Asp Ile Arg Leu Gln Gly Thr Phe Thr Pro Gly Gly Ser Ser
            725             730             735
Thr Thr Ser Thr Ile Thr Ser Ser Lys Thr Ser Thr Thr Ile Ser Thr
            740             745             750
Ser Val Thr Thr Ser Ser Ser Thr Thr Ala Lys Thr Thr Thr Thr Ser
        755             760             765
Ser Thr Thr Ser Ser Ala Gly Pro Thr Gln Thr Pro Tyr Gly Gln Cys
    770             775             780
Gly Gly Gln Gly Trp Thr Gly Pro Thr Val Cys Ser Ser Gly Trp Thr
785             790             795                         800
Cys Lys Val Thr Asn Gln Trp Tyr Ser Gln Cys Leu Gln
            805             810
```